(12) United States Patent
Szewczyk

(10) Patent No.: US 9,314,444 B2
(45) Date of Patent: Apr. 19, 2016

(54) COMPOSITION AND METHOD FOR TREATMENT OF NASH

(71) Applicant: BioKier Inc., Chapel Hill, NC (US)

(72) Inventor: Jerzy Ryszard Szewczyk, Chapel Hill, NC (US)

(73) Assignee: BioKier, Inc., Chapel Hill, NC (US)

( * ) Notice: Subject to any disclaimer, the term of this patent is extended or adjusted under 35 U.S.C. 154(b) by 0 days.

(21) Appl. No.: 14/618,576

(22) Filed: Feb. 10, 2015

(65) Prior Publication Data

US 2015/0150837 A1    Jun. 4, 2015

Related U.S. Application Data

(60) Continuation-in-part of application No. 14/020,477, filed on Sep. 6, 2013, now Pat. No. 9,006,288, which is a continuation-in-part of application No. 13/646,778, filed on Oct. 8, 2012, now Pat. No. 8,680,085, which is a division of application No. 13/143,766, filed as application No. PCT/US2010/020629 on Jan. 11, 2010, now Pat. No. 8,470,885.

(60) Provisional application No. 61/143,951, filed on Jan. 12, 2009, provisional application No. 61/293,773, filed on Jan. 11, 2010.

(51) Int. Cl.
| | |
|---|---|
| *A61K 31/19* | (2006.01) |
| *A61K 31/198* | (2006.01) |
| *A61K 9/00* | (2006.01) |
| *A61K 31/195* | (2006.01) |
| *A61K 31/202* | (2006.01) |
| *A61K 9/28* | (2006.01) |
| *A61K 9/48* | (2006.01) |

(52) U.S. Cl.
CPC ........... *A61K 31/198* (2013.01); *A61K 9/0031* (2013.01); *A61K 31/19* (2013.01); *A61K 31/195* (2013.01); *A61K 9/2806* (2013.01); *A61K 9/4891* (2013.01); *A61K 31/202* (2013.01)

(58) Field of Classification Search
USPC ........................................................ 514/557
See application file for complete search history.

(56) References Cited

U.S. PATENT DOCUMENTS

| | | | |
|---|---|---|---|
| 6,548,083 B1 | 4/2003 | Wong et al. | |
| 6,652,882 B1 | 11/2003 | Odidi et al. | |
| 7,431,943 B1 | 10/2008 | Villa et al. | |
| 7,799,782 B2 * | 9/2010 | Munson ............... | C07D 231/56 514/234.5 |
| 7,960,370 B2 | 6/2011 | Sachetto et al. | |
| 8,287,898 B2 | 10/2012 | Jandacek et al. | |
| 8,318,663 B2 | 11/2012 | Young et al. | |
| 8,383,678 B2 | 2/2013 | Sachetto et al. | |
| 2003/0203004 A1 | 10/2003 | Kelm et al. | |
| 2004/0132669 A1 | 7/2004 | Nishimura et al. | |
| 2004/0132819 A1 | 7/2004 | Auestad et al. | |
| 2006/0134208 A1 | 6/2006 | Villa et al. | |
| 2006/0159749 A1 | 7/2006 | Villa et al. | |
| 2007/0032529 A1 | 2/2007 | Takagi et al. | |
| 2007/0060759 A1 | 3/2007 | Cotticelli et al. | |
| 2007/0243253 A1 | 10/2007 | Basit et al. | |
| 2008/0038321 A1* | 2/2008 | Tsuji ..................... | A23L 1/3051 424/439 |
| 2010/0130426 A1 | 5/2010 | Young et al. | |
| 2010/0130472 A1 | 5/2010 | Young et al. | |
| 2010/0311834 A1 | 12/2010 | Manku et al. | |
| 2011/0034555 A1 | 2/2011 | Osterloh et al. | |
| 2011/0071176 A1 | 3/2011 | Rowe | |

FOREIGN PATENT DOCUMENTS

| | | |
|---|---|---|
| EP | 0302481 A2 | 2/1989 |
| EP | 0509335 A1 | 10/1992 |
| EP | 1790333 A1 | 5/2007 |
| EP | 2018159 B1 | 6/2012 |
| JP | 2006056881 A5 | 2/2006 |
| JP | 2006063064 A | 9/2006 |
| WO | 9921536 | 5/1999 |
| WO | 0076478 A1 | 12/2000 |
| WO | 02083147 A1 | 10/2002 |
| WO | 2005074718 A1 | 8/2005 |
| WO | 2006003043 A1 | 1/2006 |
| WO | 2006102653 A2 | 9/2006 |
| WO | 2007036363 A2 | 4/2007 |
| WO | 2007122374 A2 | 11/2007 |
| WO | 2007127505 A2 | 11/2007 |
| WO | 2008067219 A2 | 6/2008 |
| WO | 2008071790 A2 | 6/2008 |
| WO | 2010062861 A2 | 6/2010 |
| WO | 2010062863 A1 | 6/2010 |

OTHER PUBLICATIONS

Wischmeyer et al. "Chronic Pouchitis After Ileal Pouch-Anal Anastomosis: Responses to Butyrate and Glutamine Suppositories in a Pilot Study" Mayo Clin. Proc. 1993, vol. 68, pp. 978 981.

Deacon "Incretin-based treatment of type 2 diabetes: glucagon-like peptide-1 receptor agonists and depeptidyl peptidase-4 inhibitors." Diabetes, Obesity, and Metabolism, 9 (Suppl. 1), 2007, 23-31, Department of Biomedical Sciences, Panum Institute, University of Copenhagen, Denmark.

Toft-Nielsen MB, Damholt MB, Madsbads et al. "Determinants of the impaired secretion of glucagon-like peptide-1 in type 2 diabetic patients." J Clin Endocrinol Metab 2001;86:3717-3723.

Rask E, Olsson T, Soderberg S et al. "Impaired incretin response after a mixed meal is associated with insulin resistance in nondiabetic men." Diabetes Care 2001;24:1640-1645.

Greenfield, et al. "Oral glutamine increases circulating glucagon-like peptide 1 glucagon, and insulin concentrations in lean, obese, and type 2 diabetic subjects." American Journal of Clinical Nutrition, Epub Dec. 3, 2008, vol. 89, No. 1, pp. 106-113, ISSN 1938-3297 (electronic).

(Continued)

*Primary Examiner* — Rei-Tsang Shiao
(74) *Attorney, Agent, or Firm* — James G. Passé; Passé Intellectual Property, LLC

(57) ABSTRACT

The present invention relates to a method of treating NASH or NAFLD by delivery of an effective amount of a composition comprising L-glutamine or butyric acid formulated for release in the colon by bypassing the upper digestive tract and stomach.

10 Claims, No Drawings

(56) References Cited

OTHER PUBLICATIONS

F. Reimann, et al. "Glutamine potently stimulates glucagon-like peptide-1 secretion from GLUTag cells." Diabetologia 2004 vol. 47, pp. 1592-1601, ISSN 0012-186X.

Li Li et al. "Combination of GLP-1 and sodium butyrate promote differentiation of pancreatic progenitor cells into insulin-producing cells." Tissue and Cell, 2008, vol. 40, pp. 437-445, ISSN 0040-8166.

Wendling A, Wudyka A. "Narcotic addiction following gstric bypass surgery—a case study." Obes. Surg. May 2011;21(5):680-3. PMID: 20473721 [PubMed—indexed for MEDLINE].

Tolhurst et al. "Nutritional regulation of glucagon-like peptide-1 secretion." DIO: 10.1113/jphysiol.2008.164012. J Physiol 587.1 (2009) pp. 27-32.

Spencer, "Alcohol addiction risk after bariatric surgery?" The Wall Street Journal, Jul. 18, 2006.

Saules et al. ,"Bariatric surgery history among substance abuse treatment patients: prevalence and associated features", Elsevier, Oct. 19, 2009.

Greenberg et al. "Behavioral and Psychological care in Weight Loss Surgery: Best Practice Update, Intervention and Prevention," The Lehman Series, vol. 17, No. 5, May 2009.

Odom et al., "Behavioral Predictors of Weight Regain after Bariatric Surgery," Feb. 28, 2009.

Bupropion, Wikipedia, http://en.wikipedia.org/wiki/Bupropion, May 30, 2009.

Gadde et al., "Bupropion for Weight Loss: An Investigation of Efficacy and Tolerability in Overweight and Obese Women," Obesity Research, vol. 9, No. 9, Sep. 2001.

Category: Dopamine reuptake inhibitors, Wikipedia, http://en.wikipedia.org/wiki/Category: Dopamine_reuptake_inhibitors, May 30, 2009.

Leahey et al., "Effects of bariatric surgery on food cravings: do food cravings and the consumption of craved foods 'normalize' after surgery?" Elsevier, 2012.

glucagon.com, http://www.glucagon.com/index.html, Jun. 25, 2009.

Reimann et al., "Glutamine potently stimulates glucagon-like peptide-1 secretion from GLUTag cells", Diabetologia, 2004.

Thaler et al., "Hormonal and Metabolic Mechanisms of Diabetes Remission After Gastrointestinal Surgery", Endocrinology, Apr. 16, 2009.

Hirasawa et al., "Free fatty acids regulate gut incretin glucagon-like peptide-1 secretion through GPR120", Nature Medicine, Jan. 2005, pp. 90-94, vol. 11 (1).

Higa et al, "Narcotic Withdrawal Syndrom Following Gastric Bypass—A Difficult Diagnosis", Obesity Surgery, pp. 631-634, 2011.

Appelhans, "Neurobehavioral Inhibition of Reward-driven Feeding: Implications for Dieting and Obesity", Behavior and Psychology, vol. 17, No. 4, Apr. 2009, www.obesityjournal.org.

Category: Norepinephrime reuptake inhibitors, Wikipedia, http://en.wikipedia.org/Category:Norepinephrine_reuptake_inhibitors, May 30, 2009.

Song et al., "Nutritional and Psychological Considerations after Bariatric Surgery", Aesthetic Surgery Journal, vol. 28, No. 2, Mar./Apr. 2008, pp. 195-199.

Yamaguchi et al., "Pharmacokinetic and pharmacodynamic interaction of vildagliptin and voglibose in Japanese patients with Type 2 diabetes", International Journal of Clinical Pharmacology and Therapeutics, 2013, pp. 641-651, vol. 51.

Cummings et al., "In vivo studies of amylose- and ethylcellulose-coated [13C] glucose microspheres as a model for drug delivery to the colon", Journal of Controlled Release, 1996, pp. 123-131, vol. 40, Elsevier Science B.V.

BioKier Inc., Search Report and Written Opinion Corresponding PCT Application No. 2010/020629.

Sarwer et al., "Psychosocial and Behavioral Aspects of Bariatric Surgery," Obesity Research, vol. 13, No. 4, Apr. 2005, pp. 639-648.

Kalarchian et al., "Psychiatric Disorders Among Bariatric Surgery Candidates: Relationship to Obesity and Functional Health Status", Am. J. Psychiatry 2007; 164: 328-334; Feb. 2007.

Marcus et al., "Psychiatric Evaluation and Follow-Up of Bariatric Surgery Patients", Treatment in Psychiatry, Am. J. Psychiatry 166:3, Mar. 2009.

Sarwer et al., "Psychological Issues Following Bariatric Surgery", Primary Psychiatry, Aug. 2008, pp. 50-55.

"Substance Abuse", Obesity (2009), 17, 880-884, doi: 10.1038/oby.2008.571.

Wellbutrin, Drugs.com, http://www.drugs.com/wellbutrin.html, May 28, 2009.

Samocha-Bonet et al. "Glutamine Reduces Postprandial Glycemia and Augments the Glucagon-Like Peptide-1 Response in Type 2 Diabetes Patients", The Journal of Nutrition, Jul. 2011, p. 1233-8; vol. 141(7) US.

Karaki et al., "Short-chain fatty acid receptor, GPR43, is expressed by enteroendocrine cells and mucosal mast cells in rat intestine," Cell Tissue Res, 2006, 324: 353-360m, Springer-Verlag.

San-Miguel et al., "Glutamine Prevents Fibrosis Development in Rats with Colitis Induced by 2,4,6-Trinirobenzene Sulfonic Acid," The Journal of Nutrition—Biochemical, Molecular, and Genetic Mechanisms, Jan. 22, 2010, pp. 1065-1071.

Zhou et al., "Dietary resistant starch upregulates total GLP-1 and PYY in sustained day-long manner through fermentation in rodents," Am. J. Physiological Endocrinal Metab., 2008, 295 E1160-E1166.

Katsuma et al., "Bile acids promote glucagon-like peptide-1 secretion through TGR5 in a murine enteroendocrine cell line STC-1", Biochemical and Biophysical Research Communications, 2005, vol. 329, pp. 386-390.

Hirasawa et al., "Ligand identification and functional analysis for orphan GPCR GPR120", Journal—Pharmaceutical Society of Japan, 2005, vol. 125, pp. 122-123.

Milojevic et al., "Amylose as a coating for drug delivery to the colon: Preparation and in vitro evaluation using glucose pellets", Journal of Controlled Release, 1996, vol. 38, pp. 85-94.

Wilson et al., "Exploiting gastronintestinal bacteria to target drugs to the colon: An in vitro study using amylose coated tables", International Journal of Pharmaceutics, 2005, vol. 300, pp. 89-94.

Ibekwe et al., "A new concept in colonic drug targeting: a combined pH-responsive and bacterially-triggered drug delivery technology", Alimentary Pharmacology and Therapeutics, 2008, 28, pp. 911-916.

Sinha et al., "Coating polymers for colon specific drug delivery: A comparative in vitro evaluation", Acta Pharm., 2003, 53, pp. 41-47.

Minami et al., "Colon-Specific Drug Delivery Based on a Cyclodextrin Prodrug: Release Behavior of Biphenylylacetic Acid from Its Cyclodextrin Conjugates in Rat Intestinal Tracts after Oral Administration", Journal of Pharmaceutical Sciences, Jun. 1998, vol. 87, No. 6, pp. 715-720.

Rubinstein et al., "The rationale for peptide drug delivery to the colon and the potential of polymeric carriers as effective tools", Journal of Controlled Release, 1997, vol. 46, pp. 59-73.

Krishnamachari et al., "Development of pH- and time-dependent oral microparticles to optimize budesonide delivery to ileum and colon", International Journal of Pharmaceutics, 2007, vol. 338, pp. 238-247.

Chourasia et al., "Polysaccharides for Colon Targeted Drug Delivery", Drug Delivery, 2004, 11, pp. 129-148.

Heinberg et al., "Alcohol and bariatric surgery: review nd suggested recommendations for assessment and management", Surgery for Obesity and Related Diseases, 2012, 8, pp. 357-363.

Ferguson et al., "Production of short-chain fatty acids following in vitro fermentation of saccharides, saccharide esters, fructo-oligosaccharides, starches, modified starches and non-starch saccharides", Journal of the Science of Food and Agriculture, 2000, vol. 80, pp. 166-170.

Dechelotte et al., "Absorption and metabolic effects of enterally adminstered glutamine in humans", The American Journal Physiological Society 260, 1991, 91, G677-G682.

"Fatty Liver Disease: Symptoms, Causes, and Treatments", Hepatitis Health Center, http://www.webmd.com/hepatitis/fatty-liver-disease, Aug. 4, 2014.

"Nonalcoholic Steatohepatitis (NASH) Causes, Symptoms, Treatments", Digest Disorders Health Center, Nonalcoholic Steatohepatitis (NASH)—Overview, http://www.webmd.com/digest-disorders/tc/nonalcoholic-steatohepatitis-nash-overview, Aug. 4, 2014.

(56) References Cited

OTHER PUBLICATIONS

Ibekwe, et al., "A new concept in colonic drug targeting: a combined pH-responsive and bacterially-triggered drug delivery technology", Alimentary Pharmacology & Therapeutics 28, Journal Compilation Blackwell Publishing Ltd., doi: 10.1111/j.1365-2036.2008.03810.x, pp. 911-916, 2008.

* cited by examiner

COMPOSITION AND METHOD FOR TREATMENT OF NASH

This application is a Continuation-In-Part of U.S. non-provisional application Ser. No. 14/020,477 filed on Sep. 6, 2013 which is a Continuation-In-Part of U.S. non-provisional application Ser. No. 13/646,778 filed on Oct. 8, 2012 which is a divisional of U.S. application Ser. No. 13/143,766 filed on Jul. 8, 2011 which is a 371 of PCT application PCT/US10/20629 filed on Jan. 11, 2010 which claims priority of U.S. provisional application 61/143,951 filed on Jan. 12, 2009 and U.S. provisional application 61/293,773 filed on Jan. 11, 2010 and are all included herein in their entirety by reference.

COPYRIGHT NOTICE

A portion of the disclosure of this patent contains material that is subject to copyright protection. The copyright owner has no objection to the reproduction by anyone of the patent document or the patent disclosure as it appears in the Patent and Trademark Office patent files or records, but otherwise reserves all copyright rights whatsoever.

BACKGROUND OF THE INVENTION

1. Field of the Invention

The present invention relates to a novel method and composition for treating Nonalcoholic Steatohepatitis (NASH) and Nonalcoholic Fatty Liver Disease (NAFLD). In particular, the present invention relates to the treatment of NASH and NAFLD by delivering specific naturally occurring compounds to the lower gut (colon) or rectum.

2. Description of Related Art

Butyric acid and propionic acid are naturally occurring fatty acids that occur in the form of esters in animal fats and plant oils. For example, the triglyceride of butyric acid makes up 3% to 4% of butter. Butyric acid is found in rancid foods, such as butter and cheese, and has a very unpleasant smell and taste. Butyric acid and propionic acid are important members of the fatty acid sub-group called the short-chain fatty acids.

Glutamine is natural amino acid that is used as a nutritional supplement in the treatment of a variety of diseases, including cancer. Glutamine is the most abundant free amino acid in the human body and, in addition to its role as a component of protein, it serves a variety of functions in the body. It is a non-essential amino acid because it is made by body cells. In addition, most dietary proteins contain ample amounts of glutamine and healthy people usually obtain all the additional glutamine that they need in their diet.

Glutamine, butyric acid, propionic acid and their salts are difficult to administer unformulated by the oral route to the lower gut as they are absorbed in the upper large intestine, if not degraded by stomach acids or conditions in the stomach or small intestine, first. These compounds are agonists of L-cells in the colon, which they stimulate to cause secretion of gut hormones. When dosed orally and unformulated the minimum effective amount of these compounds is 30 grams. Doses of 30 grams and more are toxic, in the case of glutamine, or unpalatable due to unpleasant smell and taste, in the case of butyrate propionate.

NASH is a common, often "silent", liver disease. It resembles alcoholic liver disease, but occurs in people who drink little or no alcohol. The major feature in NASH is fat in the liver, along with inflammation and damage. Most people with NASH feel well and are not aware that they have a liver problem. Nevertheless, NASH can be severe and can lead to cirrhosis in which the liver is permanently damaged and scarred and no longer able to function properly.

NAFLD is a fatty liver disease common in chronic liver disease subjects. Excess liver fat can lead to liver complications. While not alcohol-related, these conditions can be related to obesity, diet, and other health-related issues.

Individuals with elevated liver enzymes and/or one having a fatty liver (e.g. determined by ultrasound or fatty liver index) are considered to have NASH or NAFLD. A reduction in enzymes, fat, or fatty liver index is an indicator of an improving or corrected condition.

There are a number of compositions designed to deliver a medicament to the lower gut. One in particular is a coating designed to release in both the pH and bacterial environment of the colon, covered by U.S. patent application Ser. No. 11/735,248, incorporated herein by reference including all related patents and applications.

A number of other formulations are available for delivery of desired compositions to the colon, including amylose-coated tablets, enterically coated chitosan tablets, matrix-within-matrix or multimatrix systems, or polysaccharide-coated tablets. One other example of multimatrix controlled-release systems is disclosed in U.S. Pat. No. 7,431,943 issued Oct. 7, 2008 to Villa et al. and incorporated herein by reference. Disclosed is a matrix-within-matrix design wherein a lipophilic phase and amphiphilic phase are incorporated within the inner matrix and at least a portion of the active ingredient is incorporated into the amphiphilic phase. Others include those described in EP 2,018,159, where a drug is released by bacteria and/or pH by removing a coating in the colon. Essentially, these compositions bind, block, encapsulate, or coat access to the drug within but are dissolved in the unique pH or bacterial environment of the colon to make a drug bioavailable in the colon.

BRIEF SUMMARY OF THE INVENTION

The present invention relates to the discovery that certain naturally occurring compositions can be delivered to the colon or rectum by bypassing the stomach and upper digestive system. These compositions increase the production of gut hormones, especially GLP-1 which, among other effects, results in the lowering of liver enzymes, liver fat content, and fatty liver index, and which can treat NASH and NAFLD. It also relates to the discovery that, with this delivery method, L-glutamine and butyric acid are surprisingly effective, while there are no reports that the oral administration of unformulated (including present in foods) glutamine, butyric, or propionic acids demonstrate such activity.

Accordingly, in one embodiment, the invention is a method of treating or preventing NASH or NAFLD comprising:
  a) selecting a composition comprising a composition from the group consisting of L-glutamine or butyric acid, the composition formulated to release in a colon-targeted delivery system or in a rectal-release system; and
  b) administering at least one of L-glutamine or butyric acid compositions to the individual sufficient to achieve the desired result.

DETAILED DESCRIPTION OF THE INVENTION

While this invention is susceptible to embodiment in many different forms there are, shown in the drawings and herein described in detail, specific embodiments, with the understanding that the present disclosure of such embodiments is to be considered as an example of the principles and not intended to limit the invention to the specific embodiments shown and described. In the description below, like reference numerals are used to describe the same, similar, or corresponding parts in the several views of the drawings. This detailed description defines the meaning of the terms used herein and specifically describes embodiments in order for those skilled in the art to practice the invention.

The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

References throughout this document to "one embodiment", "certain embodiments", and "an embodiment" or similar terms means that a particular feature, structure, or characteristic described in connection with the embodiment is included in at least one embodiment of the present invention. Thus, the appearances of such phrases in various places throughout this specification are not necessarily all referring to the same embodiment. Furthermore, the particular features, structures, or characteristics may be combined in any suitable manner in one or more embodiments without limitation.

The term "or", as used herein, is to be interpreted as an inclusive or meaning any one or any combination. Therefore, "A, B, or C" means any of the following: "A; B; C; A and B; A and C; B and C; A, B, and C". An exception to this definition will occur only when a combination of elements, functions, steps, or acts are in some way inherently mutually exclusive.

The drawings featured in the figures, if any, are for the purpose of illustrating certain convenient embodiments of the present invention, and are not to be considered as limitations thereto. The term "means" preceding a present participle of an operation indicates a desired function for which there is one or more embodiments, i.e., one or more methods, devices, or apparatuses for achieving the desired function and that one skilled in the art could select from these or their equivalent in view of the disclosure herein and use of the term "means" is not intended to be limiting.

As used herein, the term "treating" refers to alleviating the specified condition, eliminating or reducing the symptoms of the condition, slowing or eliminating the progression of the condition, and preventing or delaying the initial occurrence of the condition in a subject or reoccurrence of the condition in a previously afflicted subject.

As used herein, a "condition or disorder" refers to any NASH or NAFLD disease state, a particular state of a mammal, such as a human, or the like, to which at least one of a decrease in elevated liver enzymes, a decrease in fat in the liver, or a reduction in the liver index would serve to treat or prevent NASH or NAFLD. In one embodiment, the mammal is a human. Conditions for treatment include, but are not limited to, NASH and NAFLD.

While L-glutamine and butyric and propionic acids are known to induce secretion of gut hormones from cell lines derived from L-cells, the oral route of administration in vivo is not known to induce secretion of gut hormones. When the upper gut is bypassed and delivery is directly to the colon, as demonstrated by direct colonic delivery, an increase in secretion of GLP-1 and PYY from the colon is observed. "In rats it was demonstrated that butyrate formed from carbohydrates via fermentation in the rat colon reduces fat in the rat liver". In human diabetic subjects it was demonstrated that colon delivered L-glutamine increased secretion of GLP-1

The compounds of the invention for stimulating gut hormone release are natural compounds, selected from the group comprising L-glutamine or butyric acid in any form, such as precursors, salts, or the like. It is understood that this includes combinations of the compounds with other treatments for the condition, as well as L-glutamine and butyric acid individually.

As used herein, "a compound" of the present invention includes all L-glutamine and butyric acid compounds and their forms described herein.

The compounds of the present invention may crystallize in more than one form, a characteristic known as polymorphism, and such polymorphic forms ("polymorphs") are within the scope of the present invention. Polymorphism generally can occur as a response to changes in temperature, pressure, or both. Polymorphism can also result from variations in the crystallization process. Polymorphs can be distinguished by various physical characteristics known in the art, such as x-ray diffraction patterns, solubility, and melting point.

Certain of the compounds described herein contain one or more chiral centers, or may otherwise be capable of existing as multiple stereoisomers. The scope of the present invention includes mixtures of stereoisomers, as well as purified enantiomers or enantiomerically/diastereomerically enriched mixtures. Also included within the scope of the invention are the individual isomers of the compounds of the present invention, as well as any wholly or partially equilibrated mixtures thereof. The present invention also includes the individual isomers of the compounds represented by the formulas above as mixtures with isomers, thereof, in which one or more chiral centers are inverted.

Typically, but not absolutely, the compounds herein include the salts of the present compositions and include the pharmaceutically acceptable salts. Salts encompassed within the term "pharmaceutically acceptable salts" refer to non-toxic salts of the compounds of this invention. Salts of the compounds of the present invention may include acid-addition salts. Representative salts include acetate, benzenesulfonate, benzoate, bicarbonate, bisulfate, bitartrate, borate, calcium edetate, camsylate, carbonate, clavulanate, citrate, dihydrochloride, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, sulfate, tannate, tartrate, teoclate, tosylate, thethiodide, thmethylammonium, and valerate salts. Other salts, which are not pharmaceutically acceptable, may be useful in the preparation of compounds of this invention, and these should be considered to form a further aspect of the invention.

The "administering" of the L-glutamine or butyric acid composition of the present invention can refer to oral, rectal, or the like, for delivery direct to the colon, and is not dependent on any particular means of administration. As described elsewhere herein, the compounds are so formulated to be taken rectally or taken so as to bypass the upper digestive tract and stomach to deliver the composition to the colon.

As used herein, the term "effective amount" means that amount of a drug or pharmaceutical agent that will elicit the biological or medical response of a tissue, system, animal, or human that is being sought, for instance, by a researcher or clinician.

The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. A therapeutically effective amount will produce a "therapeutic effect".

For use in therapy, therapeutically effective amounts of a compound of the present invention, as well as salts thereof, are presented as a pharmaceutical composition formulated to release in a colon-targeted delivery system.

The present invention provides pharmaceutical compositions that include effective amounts of L-glutamine or butyric acid as herein described, or a salt thereof, and one or more pharmaceutically acceptable carriers, diluents, or excipients. Using the term "L-glutamine" or "butyric acid" includes the salt carriers, diluents, excipients, or the like. The carrier(s), diluent(s), or excipient(s) must be acceptable, in the sense of being compatible with the other ingredients of the formulation, and not deleterious to the recipient of the pharmaceutical composition and consistent with the mode of administration, i.e., oral or rectal for delivery to the colon.

In accordance with another aspect of the invention, there is also provided a process for the preparation of a pharmaceutical formulation, including admixing a compound of the present invention or salts thereof, with one or more pharmaceutically acceptable carriers, diluents, or excipients.

A therapeutically effective amount of a compound of the present invention will depend upon a number of factors. For example, the species, age, and weight of the recipient, the precise condition requiring treatment and its severity, the nature of the formulation, and the type of colon-targeted delivery system, are all factors to be considered. The therapeutically effective amount ultimately should be at the discretion of the attendant, physician, or veterinarian. Regardless, an effective amount of L-glutamine or butyric acid compound of the present invention for the treatment of humans and animals suffering from NASH and NAFLD and associated conditions, generally, should be in the range of 0.01 to 100 mg/kg body weight of recipient (mammal) per day. More often, the effective amount should be in the range of 0.3 to 30 mg/kg body weight per day. Thus, for a 70 kg adult mammal the actual amount per day would usually be from 21 to 2100 mg. This amount may be given in a single dose per day or in a number (such as two, three, four, five, or more) of sub-doses per day such that the total daily dose is the same. An effective amount of a salt or solvate thereof may be determined as a proportion of the effective amount of the compound of the present invention per se. Similar dosages should be appropriate for treatment of the other conditions referred to herein.

Pharmaceutical formulations may be presented in unit dose forms containing a predetermined amount of active ingredient per unit dose. Such a unit may contain, as a non-limiting example, 0.5 mg to 1 g of a compound of the present invention, depending on the condition being treated, the route of administration, and the age, weight, and condition of the patient. Preferred unit dosage formulations are those containing a daily dose or sub-dose, as herein above recited, or an appropriate fraction thereof, of an active ingredient. Such pharmaceutical formulations may be prepared by any of the methods well known in the pharmacy art.

The compounds of the present invention are formulated to release in the colon using, for example (but not limited to), compositions having both a pH- and bacteria-triggered release and osmotic delivery compositions. Other colon delivery compositions include those containing polysaccharides, such as chitosan, pectin, chondroitin sulphate, cyclodexthn, dextrans, guar gum, inulin, amylose, and locust bean gum. The compounds may also be coupled with soluble polymers. Such polymers can include polyvinylpyrrolidone (PVP), pyran copolymer, polyhydroxypropylmethacrylamide-phenol, polyhydroxyethyl-aspartamidephenol, or polyethyleneoxidepolylysine substituted with palmitoyl residues. Furthermore, the compounds may be coupled to a class of biodegradable polymers; for example, polylactic acid, polyepsilon caprolactone, polyhydroxy butyric acid, polyorthoesters, polyacetals, polydihydropyrans, polycyanoacrylates, and cross-linked or amphipathic block copolymers of hydrogels. In one embodiment, the present invention includes a multimatrix-targeted system, such as a targeted matrix-in-matrix system comprising a formulation of a hydrophilic first matrix, comprising a lipophlic phase and an amphiphilic phase, wherein the lipophilic phase and the amphiphilic phase are in a second matrix together and the second matrix is dispersed throughout the hydrophilic first matrix and wherein the pharmaceutical composition containing the compound is at least partially incorporated into the amphiphilic phase. Examples of some of the matrix-in-matrix formulations are disclosed in U.S. Pat. No. 7,431,943, noted above. Those skilled in the art will appreciate the use of such compositions for the purposes of targeting delivery of the compounds of the present invention, or a salt thereof, to the colon of the subject being treated. The methods for the formulation of such compositions for targeted delivery are within the skill in the art, in view of this disclosure.

Another colon-targeted delivery system involves a pH-responsive and bacteria-triggered delivery technology (Phloral™ U.S. patent application Ser. No. 11/735,248 and EP 2,018,159 both incorporated here by reference). These compositions comprise a particle with a core and a coating for the core, the core comprising a drug and the coating comprising a mixture of a first material which is susceptible to attack by colonic bacteria and a second material which has a pH threshold of pH5 or more.

The compounds of the present invention or a salt thereof may be employed alone or in combination with other therapeutic agents. The compound(s) of the present invention and the other pharmaceutically active agent(s) may be administered together or separately and, when administered separately, administration may occur simultaneously or sequentially, in any order. The amounts of the compound(s) of the present invention and the other pharmaceutically active agent(s) and the relative timings of administration will be selected in order to achieve the desired combined therapeutic effect. The administration of a combination of a compound of the present invention or a salt or solvate thereof with other treatment agents may be in combination by administration concomitantly in: (1) a unitary pharmaceutical composition, including both compounds; or (2) separate pharmaceutical compositions, each including one of the compounds. Alternatively, the combination may be administered separately in a sequential manner wherein one treatment agent is administered first and the other second or vice versa. Such sequential administration may be close in time or remote in time.

The compounds may also be formulated in rectal compositions such as suppositories or retention enemas, e.g., containing conventional suppository bases such as cocoa butter or other glycerides. The compositions so formulated will be designed to give an effective dosage to the colon in addition to other areas a rectal administration might affect.

The compounds of the present invention may be used in the treatment of NASH and NAFLD. As such, the compounds of the present invention may be used in combination with a variety of other therapeutic agents useful in the treatment of those same disorders or conditions, including diet and exercise. The compounds of the present invention may be combined with other medical therapies to treat and/or prevent NASH, NAFLD, and associated disorders and conditions.

EXAMPLES

Example 1

1 g of butyric acid salt (for example: sodium, calcium etc.) is dispersed in suitable excipient(s) (for example: high-molecular weight PEG for capsules). Tablets or capsules containing butyrate are then coated with a layer of appropriate thickness of the Phloral™ coating system for dry delivery to the colon.

Example 2

1 g of L-glutamine (for example: sodium, calcium etc.) is dispersed in suitable excipient(s) (for example: high-molecular weight PEG for capsules). Tablets or capsules containing L-glutamine are then coated with a layer of appropriate thickness of the Phloral™ coating system for dry delivery to the colon.

Example 3

Tablets or capsules (containing 1 g of butyric acid) are made as described in Example 1. Thirty high-BMI patients with elevated liver enzymes (ALT, AST—an indicator of NASH or NAFLD) and fatty liver, as determined by ultrasound or fatty liver index, and results of biopsy are dosed with one Phloral™-coated butyric acid tablet or capsule TID prior to major meals (breakfast, lunch, and dinner) for 52 weeks. At the end of the treatment period levels of liver enzymes (ALT, AST) and fatty liver index are determined to be lower than at the beginning of the treatment and results of biopsy indicate an improvement in the NASH or NAFLD condition.

Example 4

Tablets or capsules (containing 1 g of L-glutamine) are made as described in Example 2. Thirty high-BMI patients with elevated liver enzymes (ALT, AST—an indicator of NASH or NAFLD) and fatty liver, as determined by ultrasound, fatty liver index and biopsy, are dosed with one Phloral™-coated L-glutamine tablet or capsule TID prior to major meals (breakfast, lunch, and dinner) for 52 weeks. At the end of the treatment period levels of liver enzymes (ALT, AST) and fatty liver index are determined to be lower than at the beginning of the treatment and results of biopsy indicate an improvement in the NASH or NAFLD condition.

What is claimed is:

1. A method of treating NASH or NAFLD comprising:
   a) selecting a composition comprising a composition from the group consisting of L-glutamine, the composition formulated to release in a colon-targeted delivery system; and
   b) administering the L-glutamine composition to the individual sufficient to achieve the desired result, wherein the L-glutamine is administrated to the individual at a daily dosage of 0.3 to 30 mg/kg of body weight.

2. A method according to claim 1 wherein the colon-targeted delivery system is a matrix-within-matrix delivery system.

3. A method according to claim 2 wherein the colon-targeted delivery system is a controlled-release formulation of a hydrophilic first matrix comprising a lipophilic phase and an amphiphilic phase wherein the lipophilic phase and the amphiphilic phase are in a second matrix together and said second matrix is dispersed throughout the hydrophilic first matrix wherein the agent is at least partially incorporated into the amphiphilic phase.

4. A method according to claim 1 wherein the targeted delivery system is a combination bacteria/pH release.

5. A method according to claim 1 wherein the administration of the composition reduces at least one of a liver enzyme, liver fat, or fatty liver index.

6. A method of treating NASH or NAFLD comprising:
   a) selecting a composition comprising a composition from the group consisting of butyric acid, the composition formulated to release in a colon-targeted delivery system or in a rectal release system; and
   b) administering the butyric acid composition to the individual sufficient to achieve the desired result, wherein the butyric acid is administrated to the individual at a daily dosage of 0.3 to 30 mg/kg of body weight.

7. A method according to claim 6 wherein the colon-targeted delivery system is a matrix-within-matrix delivery system.

8. A method according to claim 7 wherein the colon-targeted delivery system is a controlled-release formulation of a hydrophilic first matrix comprising a lipophilic phase and an amphiphilic phase, wherein the lipophilic phase and the amphiphilic phase are in a second matrix together and said second matrix is dispersed throughout the hydrophilic first matrix wherein the agent is at least partially incorporated into the amphiphilic phase.

9. A method according to claim 6 wherein the targeted delivery system is a combination bacteria/pH release.

10. A method according to claim 6 wherein the administration of the composition reduces at least one of a liver enzyme, liver fat, or fatty liver index.

* * * * *